US010859657B2

United States Patent
Gong et al.

(10) Patent No.: US 10,859,657 B2
(45) Date of Patent: Dec. 8, 2020

(54) MRI RECONSTRUCTION USING DEEP LEARNING, GENERATIVE ADVERSARIAL NETWORK AND ACQUISITION SIGNAL MODEL

(71) Applicant: The Board of Trustees of the Leland Stanford Junior University, Stanford, CA (US)

(72) Inventors: Enhao Gong, Sunnyvale, CA (US); Greg Zaharchuk, Stanford, CA (US); John M. Pauly, Stanford, CA (US); Morteza Mardani Korani, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 31 days.

(21) Appl. No.: 16/427,599

(22) Filed: May 31, 2019

(65) Prior Publication Data
US 2019/0369191 A1    Dec. 5, 2019

Related U.S. Application Data
(60) Provisional application No. 62/678,663, filed on May 31, 2018.

(51) Int. Cl.
*G01R 33/56* (2006.01)
*G06T 7/00* (2017.01)
(Continued)

(52) U.S. Cl.
CPC .......... *G01R 33/5608* (2013.01); *A61B 5/055* (2013.01); *G01R 33/483* (2013.01);
(Continued)

(58) Field of Classification Search
CPC ............ G01R 33/5608; G01R 33/4818; G01R 33/483; G06T 7/0012; G06T 2207/20081;
(Continued)

(56) References Cited

U.S. PATENT DOCUMENTS

| 2012/0262167 | A1* | 10/2012 | Lai ..................... G01R 33/5611 324/309 |
| 2017/0309019 | A1* | 10/2017 | Knoll ....................... G06T 5/00 |
| 2018/0336680 | A1* | 11/2018 | Beck ..................... G01R 33/20 |

OTHER PUBLICATIONS

Mardani et al., "Deep Generative Adversarial Networks for Compressed Sensing (GANCS) Automates MRI" arXiv:1706.00051v1 [cs.CV], Wed, May 31, 2017.
Wang et al. (Apr. 2016). Accelerating magnetic resonance imaging via deep learning. In Biomedical Imaging (ISBI), 2016 IEEE 13th International Symposium on (pp. 514-517). IEEE.
Sun et al. (2016). Deep ADMM—net for compressive sensing MRI. In Advances in Neural Information Processing Systems (pp. 10-18).
Hammernik et al. (2017). Learning a Variational Network for Reconstruction of Accelerated MRI Data. arXiv preprint arXiv:1704.00447.

(Continued)

*Primary Examiner* — Gregory H Curran
(74) *Attorney, Agent, or Firm* — Lumen Patent Firm

(57) ABSTRACT

A method for diagnostic imaging includes measuring undersampled data y with a diagnostic imaging apparatus; linearly transforming the undersampled data y to obtain an initial image estimate x̃; applying the initial image estimate x̃ as input to a generator network to obtain an aliasing artifact-reduced image x̄ as output of the generator network, where the aliasing artifact-reduced image x̄ is a projection onto a manifold of realistic images of the initial image estimate x̃; and performing an acquisition signal model projection of the aliasing artifact-reduced x̄ onto a space of consistent images to obtain a reconstructed image x̂ having suppressed image artifacts.

11 Claims, 2 Drawing Sheets

(51) Int. Cl.
*G01R 33/48* (2006.01)
*A61B 5/055* (2006.01)
*G01R 33/483* (2006.01)
*G16H 30/40* (2018.01)

(52) U.S. Cl.
CPC ........ *G01R 33/4818* (2013.01); *G06T 7/0012* (2013.01); *G16H 30/40* (2018.01); *G06T 2207/20081* (2013.01); *G06T 2207/20084* (2013.01)

(58) Field of Classification Search
CPC .......... G06T 2207/20084; G16H 30/40; A61B 5/055
See application file for complete search history.

(56) References Cited

OTHER PUBLICATIONS

Zhu et al. (2017). Image reconstruction by domain transform manifold learning. arXiv preprint arXiv:1704.08841.
Cham et al. (2017). Deep De-Aliasing for Fast Compressive Sensing MRI. arXiv preprint arXiv:1705.07137.
Schlemper, et al. A Deep Cascade of Convolutional Neural Networks for MR Image Reconstruction. In International Conference on Information Processing in Medical Imaging (pp. 647-658).
Lee, et al. (2017). Deep artifact learning for compressed sensing and parallel MRI. arXiv preprint arXiv:1703.01120.

* cited by examiner

MRI RECONSTRUCTION USING DEEP LEARNING, GENERATIVE ADVERSARIAL NETWORK AND ACQUISITION SIGNAL MODEL

CROSS-REFERENCE TO RELATED APPLICATIONS

This application claims priority from U.S. Provisional Patent Application 62/678,663 filed May, 31, 2018, which is incorporated herein by reference.

STATEMENT REGARDING FEDERALLY SPONSORED RESEARCH OR DEVELOPMENT

None.

FIELD OF THE INVENTION

The present invention relates generally to magnetic resonance imaging (MRI). More specifically, it relates to techniques for MRI reconstruction.

BACKGROUND OF THE INVENTION

Due to its superb soft tissue contrast, magnetic resonance imaging (MRI) is a major imaging modality in clinical practice. MRI image reconstruction is typically an ill-posed linear inverse problem demanding time and resource intensive computations that substantially trade off accuracy for speed in real-time imaging.

Real-time MRI acquisition, reconstruction and visualization is of paramount importance for diagnostic and therapeutic guidance. Interventional and image-guided therapies as well as interactive diagnostic tasks need rapid image preparation within a few milliseconds. This is hindered, however, by the slow acquisition process, taking several minutes to acquire clinically acceptable images. Inefficient acquisition becomes more pronounced for high-resolution and volumetric images. One possible solution is to decrease the scan duration through significant undersampling. However, such undersampling leads to a seriously ill-posed linear inverse reconstruction problem.

To render the MRI reconstruction well-posed, conventional compressed sensing (CS) incorporates the prior about the inherent low dimensionality of images by means of sparsity regularization in a proper transform domain such as Wavelet (WV), or, finite differences (or Total Variation, TV). This typically demands running iterative algorithms, for solving non-smooth optimization programs, that are time and resource intensive, and thus not affordable for real-time MRI visualization. Moreover, the sparsity assumption is rather universal and although it is useful for certain image types, it is oblivious to the inherent latent structures that are specific to each dataset.

A few attempts have been recently carried out to speed up medical image reconstruction by leveraging historical patient data, e.g., by training a network that learns the relation map between an initial aliased image and the gold-standard one. Although reconstruction speeds up, these techniques suffer from blurring and aliasing artifacts. This is mainly because they adopt a pixel-wise $l_1/l_2$ cost for training that is oblivious to structured artifacts and high-frequency texture details. These details, however, are crucial for accurately making diagnostic decisions. In addition, these techniques lack any mechanism that ensures the retrieved images are consistent with the measurements.

Deep neural networks have been used to learn image prior or sparsifying transform from historical data in order to solve a nonlinear system using iterative optimization algorithms as in the conventional CS methods. While improving the reconstruction performance, these methods incur high computational cost due to several iterations for finding the optimal reconstruction.

BRIEF SUMMARY OF THE INVENTION

To cope with these challenges, the present disclosure provides a CS framework that applies generative adversarial networks (GAN) to modeling a (low-dimensional) manifold of high-quality MR images. Leveraging a mixture of least-squares (LS) GANs and pixel-wise $l_1/l_2$ cost, a deep residual network with skip connections is trained as the generator that learns to remove the aliasing artifacts by projecting onto the image manifold. This least-squares generative adversarial network (LSGAN) learns the texture details, while $l_1/l_2$ suppresses the high-frequency noise. A discriminator network, which is a multilayer convolutional neural network (CNN), plays the role of a perceptual cost that is then jointly trained based on high quality MR images to score the quality of retrieved images.

In the operational phase, an initial aliased estimate (e.g., simply obtained by zero-filling) is propagated into the trained generator to output the desired reconstructions, that demands very low computational overheads.

Extensive evaluations on a large contrast-enhanced MR dataset of images rated by expert radiologists corroborate that this generative adversarial networks compressed sensing (GANCS) technique recovers higher quality images with fine texture details relative to conventional CS schemes as well as pixel-wise training schemes. In addition, GANCS performs reconstruction under a few milliseconds, m which is two orders of magnitude faster than state-of-the-art CS-MRI schemes. Moreover, the perceptual quality metric offered by the trained discriminator network can significantly facilitate the radiologists' quality assurance tasks.

In other contexts, generative adversarial networks (GANs) have proven successful in modeling distributions (low-dimensional manifolds) and generating natural images (high-dimensional data) that are perceptually appealing. Despite the success of GANs for local image restoration such as super-resolution and inpainting, due to fundamental differences, GANs have not been considered for correcting the aliasing artifacts in biomedical image reconstruction tasks. In essence, aliasing artifacts (e.g., in MRI) emanate from data undersampling in the frequency domain that globally impacts the entire space domain image. Nevertheless, the present approach uses GANs for MRI reconstruction. The approach uses GANs for modeling low-dimensional manifold of high-quality MR images. The images lying on the manifold are not however necessarily consistent with the observed (undersampled) data. As a result, the reconstruction deals with modeling the intersection of the image manifold and subspace of data-consistent images; such a space is an affine subspace for linear measurements. To this end, the present GANCS approach adopts a tandem network of a generator (G), an affine projection operator (A), and a discriminator (D). The generator aims to create gold-standard images from the complex-valued aliased inputs using a deep residual network (ResNet) with skip connections which retain high resolution information. The data-consistency projection builds upon the (known) signal model and performs an affine projection onto the space of data consistent images. The D network is a multilayer convolutional neural network (CNN) that is trained using both the "fake" images created by G, and the corresponding gold-standard ones, and aims to correctly distinguish fake from real. Least-squares GANs (LSGANs) is used due to their stability properties. Alternatively, other GANs frameworks may be used, where usually the differences are just cost functions, e.g., Wasserstein GAN (W-GAN), Cycle-GAN, BigGAN, or StarGAN. To control the high-frequency texture details returned by LSGANs, and to further improve the training stability, we partially use the pixel-wise $l_1$ and $l_2$ costs for training the generator.

The GANCS results have almost similar quality to the gold-standard (fully-sampled) images, and are superior in terms of diagnostic quality relative to the existing alternatives including conventional iterative CS and deep learning based methods that solely adopt the pixel-wise $l_2$-based and $l_1$-based criteria. Moreover, the reconstruction only takes around 30 ms, which is two orders of magnitude faster than state-of-the-art conventional CS toolboxes.

In one aspect, the invention provides a method for diagnostic imaging comprising: measuring undersampled data y with a diagnostic imaging apparatus; linearly transforming the undersampled data y to obtain an initial image estimate $\tilde{x}$; applying the initial image estimate $\tilde{x}$ as input to a generator network to obtain an aliasing artifact-reduced image $\check{x}$ as output of the generator network, wherein the aliasing artifact-reduced image $\check{x}$ is a projection onto a manifold of realistic images of the initial image estimate $\tilde{x}$; and performing an acquisition signal model projection of the aliasing artifact-reduced image $\check{x}$ onto a space of consistent images to obtain a reconstructed image $\hat{x}$ having suppressed image artifacts.

The diagnostic imaging apparatus may be, for example, an MRI scanner, and the undersampled data is k-space data.

Linearly transforming the undersampled data y may comprise, for example, zero padding the undersampled data y, or finding an approximate zero-filling reconstruction from the undersampled data y.

Preferably, the generator network is trained to learn the projection onto the manifold of realistic images using a set of training images X and corresponding set of undersampled measurements Y using least-squares generative adversarial network techniques in tandem with a discriminator network to learn texture details and supervised cost function to control high-frequency noise.

The supervised cost function may comprise a mixture of smooth $l_2$ cost and non-smooth $l_1$ cost.

The discriminator network may be a multilayer deep convolutional neural network.

The discriminator network may be trained using least-squares cost for a discriminator decision.

The generator network may be a deep residual network with skip connections.

In some embodiments, performing the acquisition signal model projection is implemented as part of the generator network using a soft least-squares penalty during training of the generator network.

In some embodiments, the reconstructed image $\hat{x}$ is applied to the generator network to obtain a second aliasing artifact-reduced image, and the second aliasing artifact-reduced image is projected onto the space of consistent images to obtain a final reconstructed image.

DETAILED DESCRIPTION OF THE INVENTION

Figure 1:
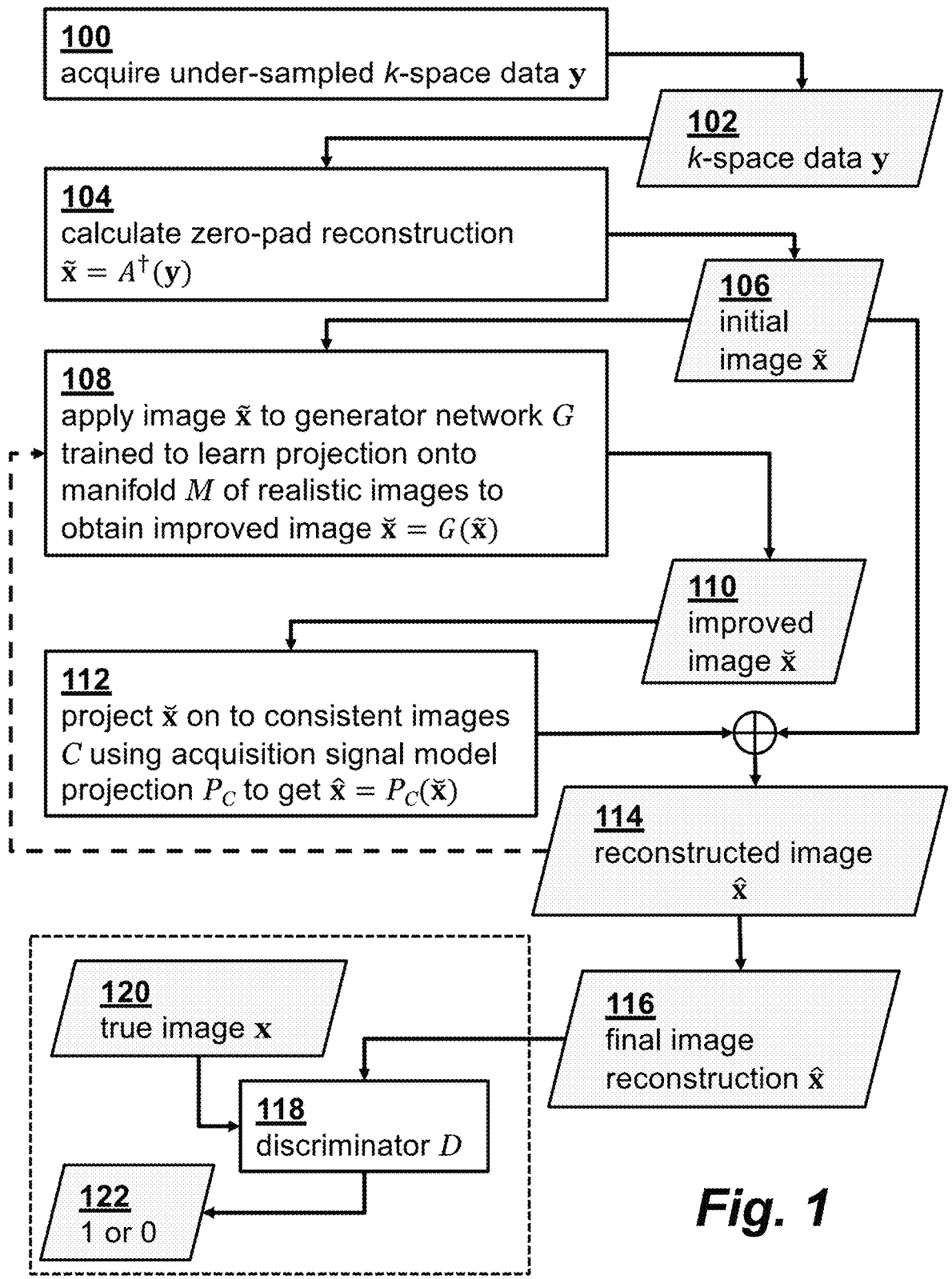
FIG. 1 is a flowchart illustrating a method for image reconstruction according to an embodiment of the invention.

Consider a generic MRI acquisition model that forms an image $x \in R^N$ from k-space projection data $y \in R^M$ $$y=A(x)+v \quad (1)$$

where the (possibly) nonlinear map A: $C^N \rightarrow C^M$ encompasses the effects of sampling, coil sensitivities, and the discrete Fourier transform (DFT). The error term $v \in R^M$ captures the noise and unmodeled dynamics. We assume the unknown (complex-valued) image x lies in a low-dimensional manifold, M. No information is known about the manifold besides the K training samples $X=\{x_k\}$ drawn from it with the corresponding K (possibly) noisy observations $Y=\{y_k\}$. The data $\{X,Y\}$ can be obtained for instance from the K past patients in the dataset that have been already scanned for a sufficient time, and their high-quality reconstruction is available. Given the training data $\{X,Y\}$, the reconstruction goal is to quickly recover the image x after collecting the undersampled measurements y. A flowchart illustrating the steps of the m reconstruction method is shown in FIG. 1., where step 100 performs an MRI acquisition to obtain the under-sampled k-space measurement data 102.

Instead of relying on simple sparsity assumption of X, the approach is to automate the image recovery by learning the nonlinear inversion map $x=A^{-1}(y)$ from the historical training data $\{X,Y\}$. To this end, we begin with an initial image estimate 106, denoted $\tilde{x}$, that is calculated in step 104 by a linear transform from undersampled measurements y and possibly contains aliasing artifacts. The initial image estimate $\tilde{x}=A^{\dagger}(y)$ may be obtained via zero-filling the missing k-space components, which is the least square solution for data-consistency, and running a single iteration of conjugate gradient. The subsequent reconstruction can then be envisioned as artifact suppression that is modelled as projection onto the manifold of high-quality images. Learning the corresponding manifold is accomplished via generative adversarial networks.

The inverse imaging problem is to find a solution at the intersection of a subspace defined by the acquisition model and the image manifold. In order to effectively learn the image manifold from the available (limited number of) training samples, the technique must ensure the trained manifold contains plausible MR images and must ensure the points on the manifold are data consistent, i.e., $y \approx A(x)$, $\forall x \in M$.

Alternating Projection with GANs for Plausible Reconstruction To ensure plausibility of the reconstruction, we use GANs. Standard GAN includes a tandem network of G and D networks. The initial image estimate $\tilde{x}=A\dagger(y)$ is applied as the input to the G network 108. The G network then projects $\tilde{x}$ onto the low-dimensional manifold M containing the high-quality images X. Let $\check{x}$ denote the output 110 of G. As will be clear later, the G net 108 is trained to learn to project to the low-dimensional manifold and achieve realistic reconstruction.

Affine Projection and Soft Penalty for Data-Consistency

The output 110 of G may not be consistent with the data. To tackle this issue, G is followed by another layer 112 that projects the output x̃ of G onto the set of data-consistent images, namely C={x:y≈A(x)} to obtain a reconstructed image 114, denoted x̂. For Cartesian grid with the linear acquisition model y=Ax, the projection is expressible as x̂=A$^{\dagger}$y+P$_N$x̃, where P$_N$=(I−A$^{\dagger}$A) resembles projection onto the null space of A. Alternatively, one can impose data consistency to the output of G through a soft least-squares (LS) penalty when training the G network, as will be seen later.

To further ensure that the reconstructed image x̂ falls in the intersection of the manifold M and the set of data-consistent images C, we can perform multiple back-and-forth projections. The network structure in FIG. 1 can then be extended by repeating the G network and P$_C$(•) in serial for a few times, or iterating steps 108 and 112 with feedback of reconstructed image x̂, as indicated by the dotted line in the figure. For simplicity of exposition, we discuss here a single back-and-forth projection. However, repeating with multiple projections shows significant performance improvement.

During training, the final reconstructed image 116 passes through the discriminator network 118 that tries to output one if x̂∈X, and zero otherwise 122. The G net 108 learns realistic reconstruction, such that D net 118 cannot always perfectly assign the right labels 122 to the real (fully-sampled) image 120 and "fake" (recovered) images 116.

Least-Squares GANs for Stable Training

Training the networks amounts to playing a game with conflicting objectives between the generator G and the discriminator D. The D network aims to score one for the real gold-standard images x, and zero for the fake/reconstructed images x̂ reconstructed by G. On the other hand, the G network also aims to map the input aliased image x̃ to a fake image x̌ that looks so realistic and plausible that it can fool D. Various strategies to reach the equilibrium mostly differ in terms of the cost function adopted for G and D networks. A standard GAN uses a sigmoid cross-entropy loss that leads to vanishing gradients which renders the training unstable, and as a result it suffers from severe degrees of mode collapse. In addition, for the generated images classified as the real with high confidence (i.e., with large decision variable), no penalty is incurred. Hence, the standard GAN tends to pull samples away from the decision boundary, which can introduce non-realistic images. Such images can hallucinate image features, and thus are not reliable for diagnostic decisions. The present method adopts an LS cost for the discriminator decision. In essence, the LS cost penalizes the decision variables without any nonlinear transformation, and as a result it tends to pull the generated samples toward the decision boundary.

Mixed Costs to Avoid High Frequency Noise

One issue with GANs is that they may overemphasize high-frequency texture, and thus ignore important diagnostic image content. In order to discard the high-frequency noise and avoid hallucination, the G net is preferably trained using a supervised $l_1/l_2$ cost as well. Such mixture with pixel-wise costs can properly penalize the noise and stabilize the training. In particular, the smooth $l_2$-cost preserves the main structure and leads to a stable training at the expense of introducing blurring artifacts. The non-smooth $l_1$-cost however may not be as stable as $l_2$ in training, but it can better discard the low-intensity noise and achieve better solutions. All in all, to reveal fine texture details while discarding noise, a mixture of LSGAN and $l_1/l_2$ cost is preferably used to train the generator. The overall procedure aims to jointly minimize the expected discriminator cost $$\min_{\Theta_d} E_x[(1-D(x;\Theta_d))^2]+E_y[D(G(\tilde{x};\Theta_g);\Theta_d)^2], \quad (P1.1)$$

where $\Theta_d$ and $\Theta_g$ are parameters of the discriminator network D, and generator network G, respectively, and the minimum is taken over $\Theta_d$, and the expected generator cost $$\min_{\Theta_g} E_y[\|y-AG(\tilde{x};\Theta_g)\Theta^2]+\eta E_{x,y}[\|x-G(\tilde{x};\Theta_g)\|_{1,2}]+ \\ \lambda E_y[(1-D(G(\tilde{x};\Theta_g);\Theta_d))^2] \quad (P1.2)$$

where the minimum is taken over $\Theta_g$, and E[•] is the statistical expectation operator, and $\|\cdot\|_{1,2}$ denotes a convex combination of the element-wise $l_1$-norm and $l_2$-norm with non-negative weights $\eta_1$ and $\eta_2$ respectively, such that $\eta_1+\eta_2=\eta$. The parameters $\Theta_d$ and $\Theta_g$ are usually weights in the CNNs and are trained based on the dataset by optimizing the above and below cost functions. Usually back-projection is used. The first LS data fidelity term in (P1.2) is also a soft penalty to ensure the direct output of G network is approximately data consistent as mentioned before. Tuning parameters λ and η also control the balance between manifold projection, noise suppression, and data consistency.

Using the cost (P1.2), taking initial estimation x̃ as input, the generator reconstructs improved x̌=G(x̃;$\Theta_g$) from k-space measurement y using the expected regularized-LS estimator, where the regularization is not based on sparsity but learned from training data via LSGAN and $l_1$-net. Different from the conventional CS scheme, which involves an iterative optimization algorithm to solve for the $l_1/l_2$-regularized LS cost, the optimization only happens in training and the optimized weights in the network can generalize to any future samples. The learned generator can be immediately applied to new test data to retrieve the image in real time. Even in the presence of LS data consistency and $l_1/l_2$ penalty, the distribution achieved by G network can coincide with the true data distribution, which ensures the reconstruction is regularized to be as designed for this manifold learning scheme: both data consistent and MRI realistic.

Network Architecture for GANCS

Figure 2:
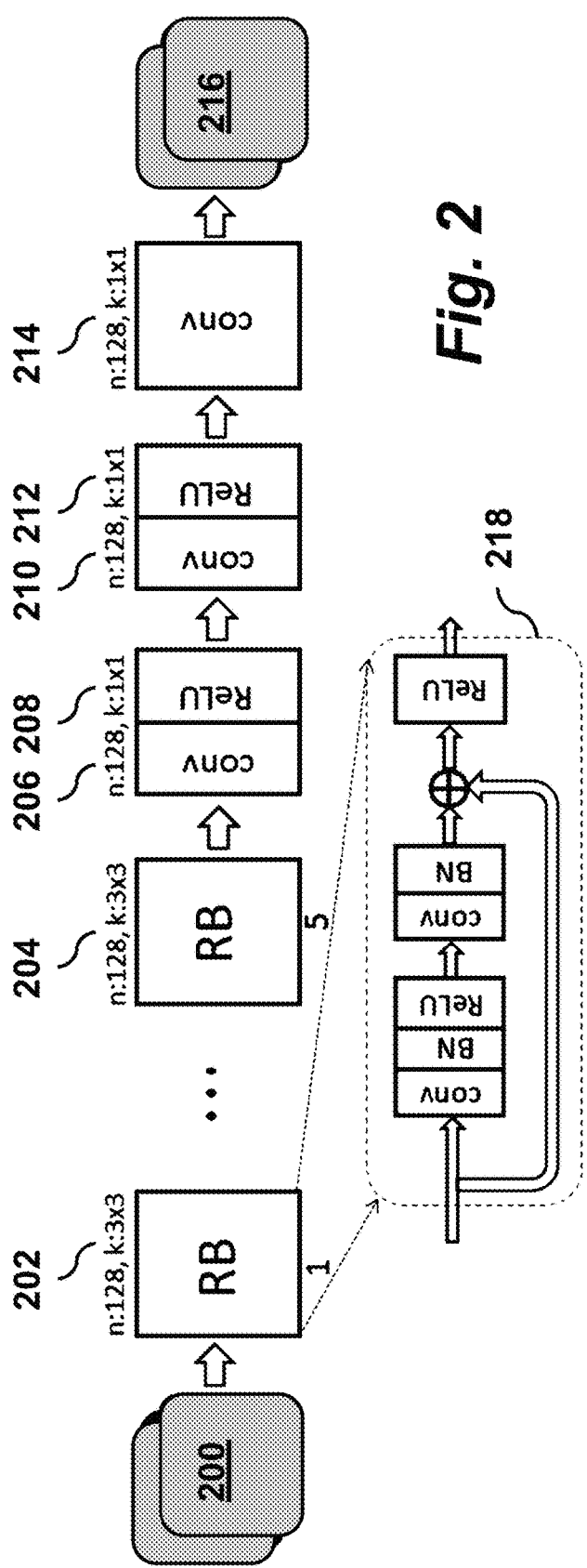
FIG. 2 is a schematic block diagram illustrating a Generator ResNet architecture with residual blocks (RB) according to an embodiment of the invention.
Figure 3:
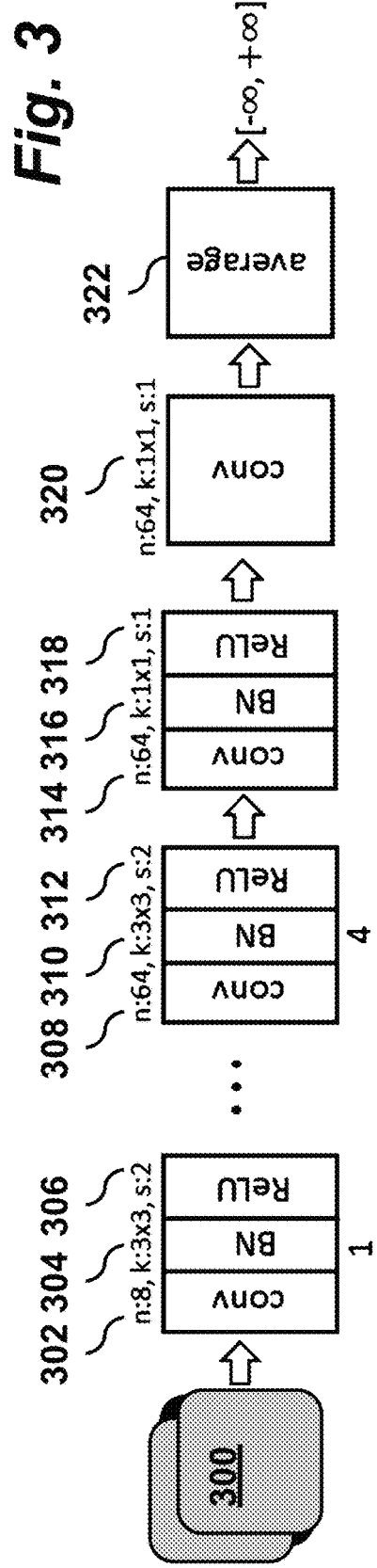
FIG. 3 is a schematic block diagram illustrating a Discriminator multilayer CNN architecture according to an embodiment of the invention.

The architectures of G and D nets are now described in relation to FIG. 2 and FIG. 3.

Residual Networks for the Generator

The input 200 and output 216 of the generator G are complex-valued images of the same size, where the real and imaginary components are considered as two separate channels. The input image x̃ is simply an initial estimate obtained, e.g., via zero-filling, which undergoes aliasing artifacts. After convolving the input channels with different kernels, they are added up in the next layer. All network kernels are assumed real-valued. A deep residual network (ResNet) is used for the generator that contains 5 residual blocks 202 through 204. As shown in the detail 218 for block 202, each block has two convolutional layers with small 3×3 kernels and 128 feature maps that are followed by batch normalization (BN) and rectified linear unit (ReLU) activation. The five residual blocks are followed by three convolutional layers with map size 1×1. The first layer has a convolution 206 and ReLU activation 208. Similarly, the second layer has a convolution 210 and ReLU activation 212, while the last layer has convolution 214 but uses no activation to return two output channels corresponding the real and imaginary image parts.

The G network learns the projection onto the manifold of realistic MR images. The manifold dimension is controlled by the number of residual blocks (RB), feature maps, stride size, and the size of discriminator. In the figure, n and k refer to number of feature maps and filter size, respectively.

Convolutional Neural Networks for Discriminator

The D network takes the magnitude of the complex-valued output of the G net and data consistency projection as an input 300. In a preferred embodiment, it is composed of a series of convolutional layers, where in all layers except the last one, a convolution operation is followed by batch normalization, and subsequently by ReLU activation. No pooling is used. Layer 1 has a convolution 302 followed by batch normalization 304 and ReLU activation 306. Similarly, layer 4 has a convolution 308 followed by batch normalization 310 and ReLU activation 312, and layer 5 has a convolution 314 followed by batch normalization 316 and ReLU activation 318. Layer 6 is a convolution 320 only, and layer 7 is an average 322. For the first four layers, the number of feature maps is doubled at each successive layer from 8 to 64, while at the same time convolution with stride 2 is used to reduce the image resolution. Kernel size 3×3 is adopted for the first 4 layers, while layers 5 and 6 use kernel size 1×1. The last layer 7 simply averages out the features to form the decision variable for binary classification. No soft-max operation is used. The variables n, k, and s in the figure refer to number of feature maps, filter size, and stride size, respectively.

Evaluations

Effectiveness of the GANCS scheme was assessed in this section for a single-coil MR acquisition model with Cartesian sampling. For the n-th patient, the acquired k-space data is denoted $y_{i,j}^{(n)} = [F(X_n)]_{i,j} + v_{i,j}^{(n)}$, where $(i,j) \in \Omega$. We adopt the single coil model for demonstration purposes, but extension to multi-coil MRI acquisition model is straightforward by simply updating the signal model. Sampling set $\Omega$ indexes the sampled Fourier coefficients. As it is conventionally performed with CS MRI, we select $\Omega$ based on a variable density sampling with radial view ordering that tends to sample more low frequency components from the center of k-space. Different undersampling rates (5 and 10) are chosen throughout the experiment. The input zero-filling (ZF) image x̃ is simply generated using inverse 2D FT of the sampled k-space, which is severely contaminated by aliasing artifacts. Input images are normalized to have the maximum magnitude unity per image.

Adam optimizer is used with the momentum parameter $\beta = 0.9$, mini-batch size 4, and initial learning rate 10-6 that is halved every 10,000 iterations. Training is performed with TensorFlow interface on a NVIDIA Titan X Pascal GPU, 12 GB RAM. We allow 20 epochs that takes around 10 hours for training.

For the dataset, abdominal image volumes were acquired for 350 pediatric patients after gadolinium-based contrast enhancement. Each 3D volume includes from 150 to 220 axial slices of size 256×128 with voxel resolution 1.07× 1.12×2.4 mm. Axial slices are used as input images for training a neural network. 340 patients (50,000 2D slices) are considered for training, and 10 patients (1,920 2D slices) for testing. All scans were acquired on a 3T MRI scanner (GE MR750).

Training Convergence

Stable convergence of GANCS was confirmed by considering evolution of different components of G and D costs for training over batches (size 4), with $\eta=0.025$ and $\lambda=0.975$ as an example to emphasize the GAN loss in training. According to (P1.2), the G cost mainly pertains to the last term which shows how well the G net can fool the D net. The D cost also includes two components based m on (P1.1) associated with the classification performance for both real and fake images. It was confirmed that all cost components decrease, and after about 5,000 batches it reaches the equilibrium cost 0.25. This implies that upon convergence the G-net images become so realistic that the D-net will behave as a flipping coin, i.e., $D(\hat{x}) = \frac{1}{2}$. In this setting with a hard affine projection layer no data-consistency cost is incurred.

It is also worth mentioning that to improve the convergence stability of GANCS, and to ensure the initial distributions of fake and real images are overlapping, we trained with pure $l_1$ cost ($\eta=1$, $\lambda=0$) at the beginning and then gradually switch to the mixture loss intended.

Quantitative Image Evaluation and Comparison

For comparison, images were reconstructed by various methods with 5-fold and 10-fold undersampling of k-space. Specifically, the gold-standard image, was compared with images reconstructed by GANCS with $l_1$-cost ($\eta=0.975$, $\lambda=0.025$), GANCS with $l_1$-cost ($\eta=1$, $\lambda=0$), GANCS with $l_2$-cost ($\eta=1$, $\lambda=0$), and CS-WV. For 5-fold undersampling, the ZF reconstruction is also included. CS reconstruction is performed using the Berkeley Advanced Reconstruction Toolbox (BART), where the tuning parameters are optimized for the best performance. These image comparisons confirmed that GANCS with $l_1$ cost ($\eta=0.975$, $\lambda=0.025$) returns the sharpest images with highest contrast and texture details that can reveal the small anatomical details. Images retrieved by GANCS with $l_2$-cost alone results in overly smooth textures as the $l_2$-cost encourages finding pixel-wise averages of all plausible solutions. Also, images obtained using GANCS with $l_1$ alone look more realistic than the $l_2$ counterpart. The reconstructed images however are not as sharp as the GANCS ($\eta=0.975$, $\lambda=0.025$) which leverages both $l_1$-net and GANs. We have observed that using m GAN alone ($\eta=0$, $\lambda=1$), the retrieved images are quite sharp with a high-frequency noise present over the image that can distort the image structure. It turns out that including the $l_1$ cost during training behaves as a low-pass filter to discard the high-frequency noises, while still achieving reasonably sharp images. It is also evident that CS-WV introduces blurring artifacts. We also tested CS-TV, but CS-WV is observed to consistently outperform CS-TV, and thus we choose CS-WV as the representative for CS-MRI.

Reconstructing 30 slices per second makes GANCS a suitable choice for real-time imaging. In terms of SNR and SSIM, GANCS with $l_1$-cost alone achieves the best performance. GANCS with proper $l_1$-cost mixing can achieve good performance with a marginally decrease from GANCS with $l_1$-cost alone.

Diagnostic Quality Assessment

The perceptual quality of resulting images was confirmed by radiologist opinion scores (ROS). The images retrieved by GANCS attain the highest score that is as good as the gold-standard.

Performance on Abnormal Cases

To address the concern that GANCS may create hallucinated images, two abnormal patients with missing left and right kidneys were scanned and images reconstructed, where the training data does not include patients with similar abnormalities. It was confirmed that GANCS misses/introduces no structures or edges.

Number of Patients for Prediction

Prediction (generalization) performance of the deep learning model heavily depends on the amount of training data. This becomes more important when dealing with scarce medical data that are typically not accessible in large scales due to privacy concerns and institutional regulations. To address this question we examined an evaluation scenario to assess the reconstruction performance for a fixed test dataset, for variable number of patients used for training. The test measured SNR versus the number of training patients for the GANCS scheme with η=0.975, λ=0.025. As the number of patients increased from 1 to 130, a noticeable SNR gain was observed. The performance gain then gradually saturates as the number of patients reaches 150. It thus seems with 150 or more patients we can take full advantage of both learning from historical data and the complexity of the networks. Recall that a fixed sampling mask is used for training and testing. GANCS, however, captures the signal model, and therefore it can easily accommodate different sampling trajectories. Also note that, if more datasets are available for training, we can further improve the model performance by increasing model complexity. Further study of the number of patients needed for other random sampling schemes and different network models is an important question that is a focus of our current research.

Discriminator Interpretation

As suggested by the training strategy, the discriminator plays a role like a radiologist that scores the quality of images created by the generator. During adversarial training, D learns to correctly discern the real fully-sampled images from the fake ones, where the fake ones become quite realistic as training progresses. It is thus insightful to understand image features that drive the quality score. To this end, we compared original images with heat maps of feature maps of D net at hidden convolutional layers. This demonstrated that, after learning from tens of thousands of generated MRI images by the G network together with the corresponding gold-standard ones, where different organs are m present, the D network learns to focus on certain regions of interest that are more susceptible to artifacts.

CONCLUSIONS

A CS framework is provided that leverages the historical data for rapid and high diagnostic-quality image reconstruction from highly undersampled MR measurements. A low-dimensional manifold is learned where the reconstructed images have not only superior sharpness and diagnostic quality, but also consistent with both the real MRI data and the acquisition model. To this end, a neural network scheme based on LSGANs and $l_1/l_2$ costs is trained, where a generator is used to map a readily obtainable undersampled image to a realistic-looking one consistent with the measurements, while a discriminator network is trained jointly to score the quality of the resulting image. The overall training acts as a game between generator and discriminator that makes them more intelligent at reconstruction and quality evaluation.

The invention claimed is:

1. A method for diagnostic imaging comprising:
    measuring undersampled data y with a diagnostic imaging apparatus;
    linearly transforming the undersampled data y to obtain an initial image estimate x̃;
    applying the initial image estimate x̃ as input to a generator network to obtain an aliasing artifact-reduced image x̌ as output of the generator network,
        wherein the aliasing artifact-reduced image x̌ is a projection onto a manifold of realistic images of the initial image estimate x̃;
    performing an acquisition signal model projection of the aliasing artifact-reduced image x̌ onto a space of consistent images to obtain a reconstructed image x̂ having suppressed image artifacts.

2. The method of claim 1 wherein the diagnostic imaging apparatus is an MRI scanner, and wherein the undersampled data is k-space data.

3. The method of claim 1 wherein linearly transforming the undersampled data y comprises zero padding the undersampled data y.

4. The method of claim 1 wherein linearly transforming the undersampled data y comprises finding an approximate zero-filling reconstruction from the undersampled data y.

5. The method of claim 1 wherein the generator network is trained to learn the projection onto the manifold of realistic images using a set of training images X and corresponding set of undersampled measurements Y using least-squares generative adversarial network techniques in tandem with a discriminator network to learn texture details and supervised cost function to control high-frequency noise.

6. The method of claim 5 wherein the supervised cost function comprises a mixture of smooth $l_2$ cost and non-smooth $l_1$ cost.

7. The method of claim 5 wherein the discriminator network is a multilayer deep convolutional neural network.

8. The method of claim 5 wherein the discriminator network is trained using a least squares cost for a discriminator decision.

9. The method of claim 1 wherein the generator network is a deep residual network with skip connections.

10. The method of claim 1 wherein performing an acquisition signal model projection is implemented as part of the generator network using a soft least-squares penalty during training of the generator network.

11. The method of claim 1 wherein the reconstructed image x̂ is applied to the generator network to obtain a second aliasing artifact-reduced image, and the second aliasing artifact-reduced image is projected onto the space of consistent images to obtain a final reconstructed image.

* * * * *